United States Patent [19]

Kühle et al.

[11] 4,318,919

[45] Mar. 9, 1982

[54] COMBATING BACTERIA WITH TETRACHLOROPHTHALAMIC ACIDS

[75] Inventors: Engelbert Kühle, Bergisch-Gladbach; Peter Kraus, Cologne; Albrecht Marhold, Leverkusen, all of Fed. Rep. of Germany

[73] Assignee: Bayer Aktiengesellschaft, Leverkusen, Fed. Rep. of Germany

[21] Appl. No.: 170,191

[22] Filed: Jul. 18, 1980

[30] Foreign Application Priority Data

Aug. 11, 1979 [DE] Fed. Rep. of Germany ....... 2932689

[51] Int. Cl.$^3$ .................... C07C 103/84; A01N 37/22
[52] U.S. Cl. .................... 424/278; 424/282; 424/319; 260/340.3; 260/340.5 R; 562/452; 562/432; 562/456
[58] Field of Search ............ 562/432, 452, 455, 456, 562/457; 71/115; 260/340.5 R, 340.3; 424/278, 319, 282

[56] References Cited

U.S. PATENT DOCUMENTS

| | | | |
|---|---|---|---|
| 2,556,665 | 6/1951 | Smith et al. | 71/115 |
| 3,507,904 | 4/1970 | Schwartz | 562/456 |
| 3,629,450 | 12/1971 | Gruenfeldet al. | 424/319 |
| 3,636,094 | 1/1972 | Yonan | 562/456 |
| 3,658,892 | 4/1972 | Martin et al. | 562/456 |
| 3,920,839 | 11/1975 | Wasley | 424/319 |
| 3,922,158 | 11/1975 | Martin et al. | 71/115 |
| 4,108,632 | 8/1978 | Bollinger et al. | 71/115 |

FOREIGN PATENT DOCUMENTS 1355849 6/1974 United Kingdom ............... 562/456

Primary Examiner—Natalie Trousof
Assistant Examiner—James H. Reamer
Attorney, Agent, or Firm—Sprung, Felfe, Horn, Lynch & Kramer

[57] ABSTRACT

Tetrachlorophthalamic acids of the formula

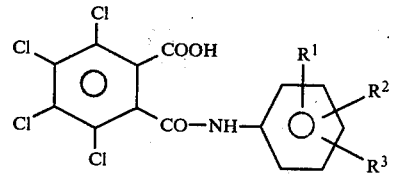

in which $R^1$ represents a trihalogenomethyl, trihalogenomethoxy or trihalogenomethylmercapto group, $R^2$ represents hydrogen, halogen or a lower alkyl or lower alkoxy group, or $R^1$ together with $R^2$, in the o-position relative to each other, denote $-O-CF_2-O-CF_2-$, $-O-CF_2-O-$ or $-O-CF_2-CFX-O-$, wherein X represents hydrogen, chlorine or fluorine, and $R^3$ represents hydrogen, halogen or a lower alkyl, lower alkoxy, lower alkylmercapto or aryloxy group, the aryloxy being optionally substituted which possess activity against bacteria, particularly those which attack plants.

9 Claims, No Drawings

COMBATING BACTERIA WITH TETRACHLOROPHTHALAMIC ACIDS

The present invention relates to certain new tetrachlorophthalamic acids, to a process for their preparation and to their use as bactericides in the protection of plants.

It has already been disclosed that certain tetrachlorophthalamic acids have a phytobactericidal activity. Thus, in the cultivation of rice, N-(2,3-dichlorophenyl)tetrachlorophthalamic acid exhibits a bactericidal action against *Xanthomonas oryzae* (see, for example, British patent specification No. 1,355,849). However, the activity is not always satisfactory when low concentrations are used.

The present invention now provides, as new compounds, the tetrachlorophthalamic acids of the general formula

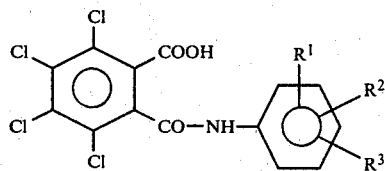

(I)

in which
R$^1$ represents a trihalogenomethyl, trihalogenomethoxy or trihalogenomethylmercapto group,
R$^2$ represents hydrogen, halogen or a lower alkyl or lower alkoxy group, or
R$^1$ together with R$^2$, in the o-position relative to each other, denote —O—CF$_2$—O—CF$_2$—, —O—CF$_2$—O— or —O—CF$_2$—CFX—O—,
wherein
X represents hydrogen, chlorine or fluorine, and
R$^3$ represents hydrogen, halogen or a lower alkyl, lower alkoxy, lower alkylmercapto or aryloxy group, the aryloxy group being optionally substituted.

The tetrachlorophthalamic acids of the present invention have powerful bactericidal actions. It is surprising that the compounds according to the invention have a better action against bacteria which are harmful to plants than the products which are known from the state of the art. The new compounds thus represent an enrichment of the art.

Preferred tetrachlorophthalamic acids of the formula (I) are those in which
R$^1$ represents a trifluoromethyl, trifluoromethoxy, trifluoromethylmercapto, difluorochloromethyl, difluorochloromethoxy or difluorochloromethylmercapto group,
R$^2$ represents hydrogen, chlorine, fluorine or a methyl or methoxy group, or
R$^1$ and R$^2$ together, in the ortho-position, represent a group —CF$_2$—O—CF$_2$—O—, —O—CF$_2$—O—, —O—CF$_2$—CF$_2$—O—, —O—CF$_2$—CFCl—O— or —O—CF$_2$—CHF—O—, and
R$^3$ represents hydrogen, chlorine or a methyl, methoxy, methylmercapto or phenoxy group, it being possible for the latter to carry one or more substituents selected from halogen, methyl groups and methoxy groups.

The present invention also provides a process for the preparation of a tetrachlorophthalamic acid of the formula (I) in which tetrachlorophthalic anhydride, of the formula

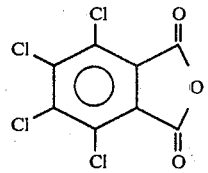

(II), is reacted with an amine of the general formula

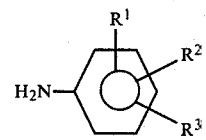

(III), in which R$^1$, R$^2$ and R$^3$ have the meanings indicated above, in the presence of a diluent.

If desired, the acids of the formula I can be converted in the corresponding salts, such as the alkali metal and the ammonium sals.

If, for example, tetrachlorophthalic anhydride and 4-trifluoromethylaniline are used as starting substances for the preparation of the compounds according to the invention, the course of the reaction can be represented by the following equation:

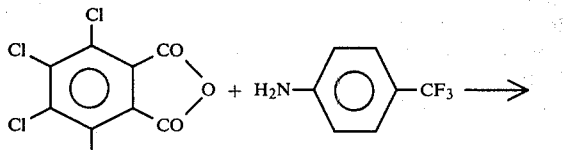

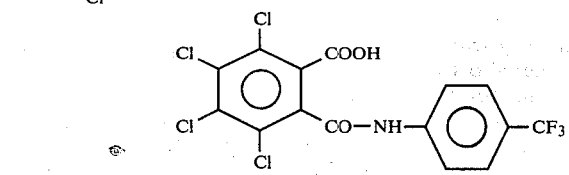

Of course, the free acids of the general formula I can be converted in suitable salts, such as alkali metal, alkaline earth metal and ammonium salts.

Tetrachlorophthalic anhydride, which is to be used as a starting substances and is characterized by the formula (II), is generally known.

The general formula (III) provides a definition of the amines also to be used as starting substances. In this formula, R$^1$, R$^2$ and R$^3$ preferably have the meanings indicated above as preferred for the general formula (I).

Amines of the formula (III) and their preparation are known and can be prepared by processes which are known from the literature (see, for example, J. Org. Chem. 25 (1960), 965 and 29 (1964), 1; Z. Obsc. Chim. (English translation) 31 (1961), 578; and Agnew. Chem. 89 (1977), 797; and see also the statements in the preparative examples). Examples of compounds of the formula (III) which may be mentioned are: 2-, 3- or 4-trifluoromethyl-aniline, 3-chloro-4-trifluoromethyl-aniline, 2-trifluoromethyl-4-methylmercapto-aniline, 3-trifluoromethyl-4-chlorophenoxyaniline, 2-, 3- or 4-trifluoromethoxy-aniline, 3-chloro-4-trifluoromethoxy-aniline, 2-, 3- or 4-trifluoromethylmercaptoaniline, 3- chloro-4-trifluoromethylmercapto-aniline, 3-chloro-4-difluorochloromethylmercapto-aniline, 5-amino-2,2-difluorobenzdioxole, 6-amino-tetrafluoro-1,3-benzdioxene and 6-amino-trifluoro-1,4-benzdioxene.

Possible diluents are any of the inert solvents. These include ethers, such as tetrahydrofuran and dioxane, hydrocarbons, such as toluene, chlorinated hydrocarbons, such as chloroform, or ketones, such as acetone.

The reaction temperatures can be varied within a substantial range, and in general the reaction is carried out between 20° and 120° C., preferably at 50° to 100° C.

Equimolar amounts of the reactants are in general used in carrying out the process, but an excess of amine up to about 10% does no harm.

Working up is effected in the customary manner. The reaction products are crystalline compounds which can be isolated by filtration.

The active compounds according to the invention exhibit a powerful microbicidal action and can be employed in practice for combating undesired microorganisms. The active compounds are suitable for use as plant protection agents.

The compounds according to the invention have a particularly good action against bactericidal diseases of plants.

Bactericidal agents are employed as plant protection for combating Pseudomonadaceae, Rhizobiaceae, Enterobacteiaceae, Corynebacteriaceae and Streptomycetaceae.

The good toleration, by plants, of the active compounds at the concentrations required for combating plant diseases permits treatment of above-ground parts of plants, of vegetative propagation stock and seeds and of the soil.

The compounds according to the invention are particularly active against bacteria of the genus Xanthomonas, for example against *Xanthomonas oryzae* in rice. The fact that the compounds according to the invention have systemic properties is of advantage in combating bacterial diseases.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g, preferably 0.01 to 10 g, are generally employed per kilogram of seed.

For the treatment of soil, active compound concentrations of 0.00001 to 0.1% by weight, preferably 0.0001 to 0.02%, are generally employed at the place of action.

The present invention also provides a bactericidal composition containing as active ingredient a compound of the present invention in admixture with a solid or liquefied gaseous diluent or carrier or in admixture with a liquid diluent or carrier containing a surface-active agent.

The present invention also provides a method of combating bacteria which comprises applying to the bacteria, or to a habitat thereof, a compound of the present invention alone or in the form of a composition containing as active ingredient a compound of the present invention in admixture with a diluent or carrier.

The present invention further provides crops protected from damage by bacteria by being grown in areas in which immediately prior to and/or during the time of the growing a compound of the present invention was applied alone or in admixture with a diluent or carrier.

It will be seen that the usual methods of providing a harvested crop may be improved by the present invention.

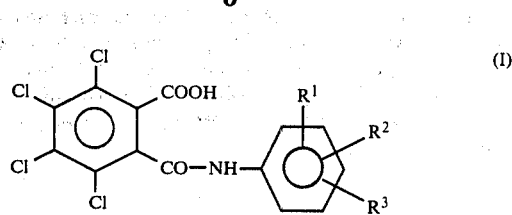

were prepared in a corresponding manner:

TABLE 1

| Compound No. | $R^1$ | $R^2$ | $R^3$ | Melting point (°C.) |
|---|---|---|---|---|
| 2 | 3-$CF_3$ | H | H | 190 (decomposition) |
| 3 | 4-$CF_3$ | H | H | 210 (decomposition) |
| 4 | 4-$CF_3$ | 3-Cl | H | 160 (decomposition) |
| 5 | 3-$CF_3$ | 4-Cl | H | 275-276 |
| 6 | 3-$OCF_3$ | H | H | 155 (decomposition) |
| 7 | 4-$OCF_3$ | H | H | 210 (decomposition) |
| 8 | 4-$OCF_3$ | 3-Cl | H | 247-248 |
| 9 | 3-$SCF_3$ | H | H | 199-202 |
| 10 | 4-$SCF_3$ | H | H | 218 (decomposition) |
| 11 | 4-$SCF_3$ | 3-Cl | H | 211-212 |
| 12 | 2-$CF_3$ | H | 4-S—$CH_3$ | 210 (decomposition) |
| 13 | 3-$CF_3$ | H | 4-O—(phenyl)—Cl | 160 (decomposition) |
| 14 | 3,4-$CF_2$—O—$CF_2$—O— | | H | 262-263 |
| 15 | 3,4-O—CFCl—$CF_2$—O— | | H | 238-242 |
| 16 | 3,4-O—CHF—$CF_2$—O— | | H | 259-262 |
| 17 | 3,4-O—$CF_2$—O— | | H | 261-263 |
| 18 | 3,4-O—CHF—$CF_2$—O— | | 6-Cl | 278 |
| 19 | 3,4-O—$CF_2$—CHF—O— | | H | 236 |
| 20 | $CF_2ClO$ | H | H | 234 |

PREPARATIVE EXAMPLES

Example 1

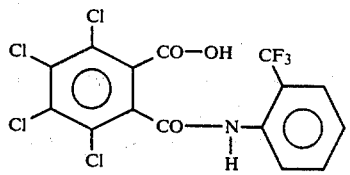

20 g (0.07 mol) of tetrachlorophthalic anhydride (melting point: 255°-257° C.) were dissolved in 100 ml of dioxane at 80° C., and 14.4 g (0.07 mol) of 2-trifluoromethylaniline in 30 ml of dioxane were added dropwise at this temperature. The mixture was heated to the boiling point for 1 hour and the reaction product was filtered off in the cold. 16 g of N-(2-trifluoromethyl-phenyl)tetrachlorophthalamic acid of melting point 205° C. (with decomposition), which corresponded to 52% of theory, were obtained.

The following compounds of the general formula

Example 2

Amines of the general formula (III) required as starting materials for some of the compounds of Table 1 could be prepared, for example, as follows:

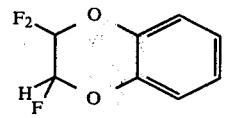

220 g of pyrocatechol and 130 of sodium hydroxide were initially introduced into 600 ml of tetramethylene sulphone at 95° to 105° C. and 330 g of trifluorochloroethylene were passed in at this temperature, while stirring. The batch was then distilled over a column under 20 mbars and a fraction of boiling point 20° to 60° C./20 mbars was collected in a well-cooled receiver. After the aqueous phase had been separated off, 332 g of pure 2,2,3-trifluoro-1,4-benzodioxene (yield: 87% of theory) of boiling point 54°-5° C./16 mbars remained; $n_D^{20} = 1.4525$.

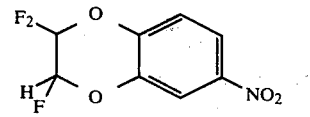

190 g of 2,2,3-trifluoro-1,4-benzodioxene were initially introduced into the reaction vessel at 5° C.; a mixture of 150 ml of nitric acid (D: 1.41) and 175 ml of concentrated sulphuric acid was added dropwise at this temperature. The mixture was subsequently stirred for 1 hour at 10° C. and then for a further hour at 20° C. and finally was warmed to 40° C. for 5 minutes. The cooled batch was poured onto 500 g of ice and the organic phase was extracted with methylene chloride. After distilling off the solvent, the residue was distilled in vacuo. 198 g of 6-nitro-2,2,3-trifluoro-1,4-benzodioxene of boiling point 100°–102° C./1.33 mbars were obtained; $n_D^{20} = 1.5078$.

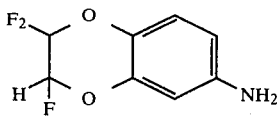

198 g of 6-nitro-2,2,3-trifluoro-1,4-benzodioxene were dissolved in 600 ml of ethanol, and 20 g of Raney nickel were added. Hydrogen was forced in under a pressure of 50 bars, while stirring, until saturation at an internal temperature of 45° C. was achieved. After letting down, the catalyst was filtered off and the filtrate was distilled. 142 g of 6-amino-2,2,3-trifluoro-1,4-benzodioxene of boiling point 125°–127° C./21 mbars, $n_D^{20} = 1.501$, were obtained.

The bactericidal activity of the compounds of this invention is illustrated by the following examples wherein the compounds according to the present invention are each identified by the number (given in brackets) from Table 1.

The known comparison compound is identified as follows:

were dissolved in 1,000 parts by weight of distilled water and the solution was sterilized at 121° C. in a closed vessel for 30 minutes.

Solvent: 40 parts by weight of dimethylformamide
Ratio of solvent to nutrient medium: 2:100.

To produce a suitable preparation of active compound, 1 part by weight of active compound was mixed with the stated amount of solvent.

The concentrate was thoroughly mixed, in the stated proportion, with the liquid nutrient medium and the mixture was poured into Petri dishes.

When the nutrient medium had cooled and solidified, the plates were inoculated with the following microorganisms and incubated at about 21° C.: *Erwinia mangiferae, Xanthomonas oryzae, Xanthomonas pelargonii, Agrobacterium tumefaciens* and *Corynebacterium michiganense.*

Evaluation was carried out after 2 to 8 days, depending on the speed of growth of the micro-organisms, the inhibition of growth compared with the untreated control being used as a measure of the action of the preparations.

The growth was evaluated using the following characteristic values (the scale rating):

1: no growth
up to 3: very strong inhibition of growth
up to 5: medium inhibition of growth
up to 7: slight inhibition of growth
9: growth equal to that of the untreated control.

The following table gives the results of the test:

TABLE 2

| Active compounds | Active compound concentration [ppm] | Agar plate test Bacterial growth (scale rating) | | | | |
|---|---|---|---|---|---|---|
| | | Erwinia mangiferae | Xanthomonas oryzae | Xanthomonas pelargonii | Agrobacterium tumefaciens | Corynebacterium michiganense |
| (A) | 500 | — | — | 9 | 9 | 9 |
| | 250 | 5 | 5 | — | — | — |
| (9) | 500 | — | — | — | 3 | 1 |
| (10) | 500 | — | — | — | 2 | 1 |
| (4) | 500 | — | — | 2 | — | 1 |
| (13) | 500 | — | — | 2 | — | 1 |
| | 250 | 1 | 1 | — | — | — |
| (11) | 500 | — | — | 1 | 1 | 1 |
| | 250 | 1 | 1 | — | — | — |
| (8) | 500 | — | — | — | 3 | 1 |

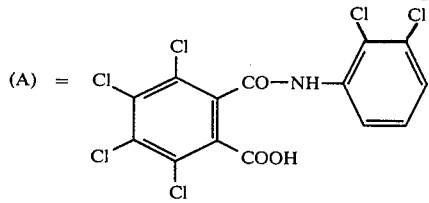

Example 3

Agar plate test

Nutrient medium used:

15 parts by weight: agar-agar
10 parts by weight: sucrose
8 parts by weight: casein hydrolysate
4 parts by weight: yeast extract
2 parts by weight: dipotassium hydrogen phosphate
0.3 part by weight: magnesium phosphate Example 4

*Xanthomonas oryzae* test/bacteriosis/rice/protective

Solvent: 25 parts by weight acetone
Emulsifier: 0.75 part by weight alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were inoculated with an aqueous suspension of *Xanthomonas oryzae* by pricking the leaves. After an incubation period of 48 hours at 100% relative atmospheric humidity, the plants remained in a greenhouse at 24° to 26° C. and 70 to 80% relative atmospheric humidity until they were evaluated.

10 days after inoculation, the infection of all the inoculated plants was evaluated in percent of the infection of the untreated control plants. 0% denoted plants with no infection, 100% denoted an infection rate comparable with the untreated control plants.

The following table gives the results of the test.

TABLE 3

| Active compounds | Xanthomonas oryzae test/bacteriosis/rice/ protective | |
|---|---|---|
| | Active compound concentration in % | Infection in % of the untreated control |
| (A) | 0.05 | 50 |
| (12) | 0.05 | 25 |
| (11) | 0.05 | 12.5 |
| (8) | 0.05 | 12.5 |
| (5) | 0.05 | 25 |

It will be appreciated that the instant specification and examples are set forth by way of illustration and not limitation, and that various modifications and changes may be made without departing from the spirit and scope of the present invention.

We claim:

1. A tetrachlorophthalamic acid of the formula

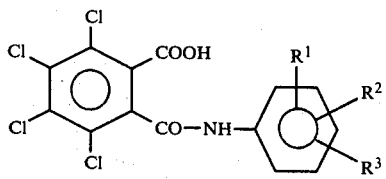

in which
R$^1$ represents a trihalogenomethyl, trihalogenomethoxy or trihalogenomethylmercapto group,
R$^2$ represents hydrogen, halogen or a lower alkyl or lower alkoxy group, or
R$^1$ together with R$^2$, in the o-position relative to each other, denote —O—CF$_2$—O—CF$_2$—, —O—CF$_2$—O— or —O—CF$_2$—CFX—O—,
X represents hydrogen, chlorine or fluorine, and
R$^3$ represents hydrogen, halogen or a lower alkyl, lower alkoxy, lower alkylmercapto or phenoxy group, the phenoxy being optionally substituted by a halogen, methyl or methoxy group.

2. A compound according to claim 1, in which
R$^1$ is a trifluoromethyl, trifluoromethoxy, trifluoromethylmercapto, difluorochloromethyl, difluorochloromethoxy or difluorochloromethylmercapto group,
R$^2$ is hydrogen, chlorine, fluorine or a methyl or methoxy group, or
R$^1$ and R$^2$ are on adjacent carbon atoms and together, are —CF$_2$—O—CF$_2$—O—, —O—CF$_2$—O—, —O—CF$_2$—CF$_2$—O—, —O—CF$_2$—CFCl—O— or —O—CF$_2$—CHF—O—, and
R$^3$ is hydrogen, chlorine or a methyl, methoxy, methylmercapto or phenoxy group, or a phenoxy group substituted by a halogen, methyl or methoxy group.

3. A compound according to claim 1, wherein such compound is N-(4-trifluoromethyl-phenyl)-tetrachlorophthalamic acid of the formula

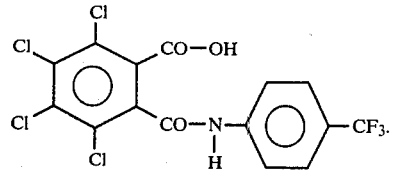

4. A compound according to claim 1, wherein such compound is N-(3-chloro-4-trifluoromethyl-phenyl)-tetrachlorophthalamic acid of the formula

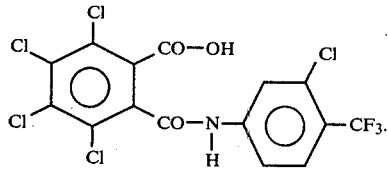

5. A compound according to claim 1, wherein such compound is N-(4-trifluoromethoxy-phenyl)-tetrachlorophthalamic acid of the formula

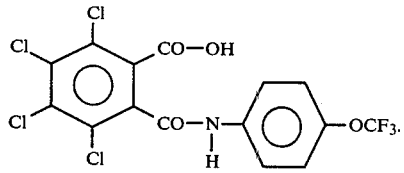

6. A compound according to claim 1, wherein such compound is N-[3,4-(1-chloro-trifluoroethylenedioxh)-phenyl]-tetrachlorophthalamic acid of the formula

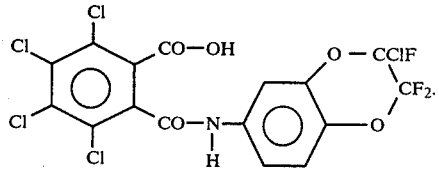

7. A bactericidal composition comprising a bactericidally effective amount of a compound according to claim 1 in admixture with a diluent.

8. A method of combating bacteria comprising applying to the bacteria, or to a habitat thereof, a bactericidally effective amount of a compound according to claim 1.

9. The method according to claim 8, wherein such compound is
N-(4-trifluoromethyl-phenyl)-tetrachlorophthalamic acid,
N-(3-chloro-4-trifluoromethyl-phenyl)-tetrachlorophthalamic acid,
N-(4-trifluoromethoxy-phenyl)-tetrachlorophthalamic acid or
N-[3,4-(1-chloro-trifluoroethylenedioxy)-phenyl]-tetrachlorophthalamic acid,
and it is applied to plants, seeds or soil.

* * * * *